United States Patent
Kohinata

(10) Patent No.: US 9,682,906 B2
(45) Date of Patent: Jun. 20, 2017

(54) METHOD FOR PURIFYING HYDROFLUOROCARBON COMPOUND

(71) Applicant: ZEON CORPORATION, Tokyo (JP)

(72) Inventor: Yuko Kohinata, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 0 days.

(21) Appl. No.: 15/103,747

(22) PCT Filed: Dec. 17, 2014

(86) PCT No.: PCT/JP2014/083406
§ 371 (c)(1),
(2) Date: Jun. 10, 2016

(87) PCT Pub. No.: WO2015/093527
PCT Pub. Date: Jun. 25, 2015

(65) Prior Publication Data
US 2016/0318832 A1    Nov. 3, 2016

(30) Foreign Application Priority Data

Dec. 20, 2013 (JP) ................................ 2013-263228

(51) Int. Cl.
*C07C 17/389* (2006.01)
*C07C 19/08* (2006.01)

(52) U.S. Cl.
CPC .................. *C07C 17/389* (2013.01)

(58) Field of Classification Search
CPC ........................... C07C 17/389; C07C 19/08
USPC ......................................................... 57/177
See application file for complete search history.

(56) References Cited

U.S. PATENT DOCUMENTS

| 5,879,581 A | 3/1999 | Ushimaru |
| 6,544,319 B1 | 4/2003 | Krouse et al. |
| 2016/0016869 A1 | 1/2016 | Sugimoto |
| 2016/0251286 A1* | 9/2016 | Sugimoto ............... C07C 19/08 |

FOREIGN PATENT DOCUMENTS

| CN | 1111669 A | 11/1995 |
| JP | 3-173799 A | 7/1996 |
| JP | 2001-247495 A | 9/2001 |
| JP | 2001-261330 A | 9/2001 |
| JP | 2002-47218 A | 2/2002 |
| JP | 2002-531538 A | 9/2002 |
| JP | 2003-261480 A | 9/2003 |
| JP | 2013-95669 A | 5/2013 |
| JP | 2014-24785 A | 2/2014 |
| WO | 00/34217 A1 | 6/2000 |
| WO | 2014/136877 A1 | 9/2014 |

OTHER PUBLICATIONS

Shirakura et al., Binder-less 3A zeolite bead adsorbent, its manufacture, and method for adsorption removal, JP 2002119849 machine translation, Apr. 2004.*
International Search Report dated Mar. 17, 2015, issued in counterpart International Application No. PCT/JP2014/083406 (2 pages).
Extended European Search Report dated Apr. 7, 2017 issued in counterpart European patent Application No. 14871549.3 (6 pages).

* cited by examiner

*Primary Examiner* — Jafar Parsa
(74) *Attorney, Agent, or Firm* — Westerman, Hattori, Daniels & Adrian, LLP

(57) ABSTRACT

The present invention is a method for purifying a linear saturated fluorohydrocarbon compound comprising bringing a crude linear saturated fluorohydrocarbon compound having four or five carbon atoms into contact with a hydrous metal salt of a synthetic crystalline aluminosilicate that has a carbon dioxide adsorption amount of 50 µmol/g or less and an average pore size of 3 Å to remove water from the crude linear saturated fluorohydrocarbon compound. The present invention makes it possible to reduce or suppress the production of a dehydrofluorinated compound due to a decomposition reaction of the linear saturated fluorohydrocarbon compound, and to remove water efficiently.

4 Claims, No Drawings

METHOD FOR PURIFYING HYDROFLUOROCARBON COMPOUND

TECHNICAL FIELD

The present invention relates to a method for purifying a fluorohydrocarbon compound. More specifically, the invention relates to a method for purifying a fluorohydrocarbon compound that can reduce or suppress the production of a dehydrofluorinated compound due to a decomposition reaction while efficiently removing water even when a crude fluorohydrocarbon compound is brought into contact with a specific molecular sieve (hereinafter may be referred to as "MS") (i.e., hydrous metal salt of synthetic crystalline aluminosilicate) using simple equipment.

BACKGROUND ART

A fluorohydrocarbon compound exhibits excellent etching selectivity with respect to the etching target material, and has been used as a dry etching gas for producing a semiconductor device.

A fluorohydrocarbon compound used in the semiconductor production field and the like must be purified to have an organic component purity of 99.90% or more and a water concentration of 50 ppm or less in order to achieve high etching selectivity. Such a fluorohydrocarbon compound may be dehydrated using an MS that is a common dehydrating agent.

However, isomerization and a decomposition reaction easily occur when a fluorohydrocarbon compound is brought into contact with an MS, whereby the purity of the fluorohydrocarbon compound may decrease.

For example, Patent Literature 1 proposes a method that purifies hexafluoro-1,3-butadiene ($C_4F_6$) using an MS having an average pore size of 5 Å. Patent Literature 1 discloses bringing hexafluoro-1,3-butadiene into contact with the MS using a circulation method, and states that hexafluoro-1,3-butadiene having a purity of at least 99.9% and a water content of 100 ppm or less can be obtained.

However, Patent Literature 1 discloses only an example in which an unsaturated fluorohydrocarbon compound having 4 carbon atoms is used.

Patent Literature 2 proposes a method for purifying a fluorohydrocarbon that includes bringing a fluorohydrocarbon compound having 4 to 8 carbon atoms into contact with an MS or alumina to reduce the hydrogen fluoride content. Patent Literature 2 states that the purity of the compound did not change due to the treatment with the MS, and the production of a decomposition product was not observed (see the examples of Patent Literature 2). Patent Literature 2 discloses 1,1,1,2,4,4,4-heptafluoro-n-butane and 1,1,1,2,2,3,5,5,5-nonafluoro-n-pentane as specific examples of the fluorohydrocarbon compound. However, Patent Literature 2 discloses only examples in which octafluorocyclopentene or 1,1,2,2,3,3,4-heptafluorocyclopentane (i.e., cyclic compound) is used, and does not disclose an example in which a linear compound is used. Paragraph 0023 of Patent Literature 2 states that "molecular sieves 4A and 5A are most preferable", and a molecular sieve 4A or 5A is used in the examples of Patent Literature 2.

Patent Literature 3 proposes a method that dehydrates a compound while suppressing the occurrence of a decomposition reaction of an organic liquid by utilizing a molecular sieve MS3A for which the amount of acid sites has been reduced to be equal to or less than a specific value through a pretreatment. However, Patent Literature 3 discloses only examples in which an alcohol compound is used.

CITATION LIST

Patent Literature

Patent Literature 1: JP-A-2003-261480 (US6,544,319B1)
Patent Literature 2: JP-A-2002-47218
Patent Literature 3: JP-T-2002-531538 (W000/34217)

SUMMARY OF INVENTION

Technical Problem

As described above, various methods have been proposed that dehydrate and purify a fluorohydrocarbon compound using an MS while suppressing a change in purity due to the treatment with the adsorbent. However, the inventor of the invention found that the content of a dehydrofluorinated compound increases when a crude linear saturated fluorohydrocarbon compound represented by $C_4H_9F$ is brought into contact with a molecular sieve MS5A according to the method disclosed in Patent Literature 1.

An object of the invention is to provide a method for purifying a fluorohydrocarbon compound that can reduce or suppress the production of a dehydrofluorinated compound due to a decomposition reaction while efficiently removing water even when a crude fluorohydrocarbon compound is brought into contact with an MS using simple equipment.

The inventor conducted extensive studies to solve the above problem. As a result, the inventor found that it is possible to reduce or suppress the production of a dehydrofluorinated compound due to a decomposition reaction of a fluorohydrocarbon compound while efficiently removing water by utilizing an MS having a carbon dioxide adsorption amount equal to or less than a specific value and having a specific average pore size. This finding has led to the completion of the invention.

Solution to Problem

One aspect of the invention provides a method for purifying a linear saturated fluorohydrocarbon compound (hereinafter may be referred to as "purification method") including bringing a crude linear saturated fluorohydrocarbon compound represented by $C_4H_9F$ or $C_5H_{11}F$ into contact with a hydrous metal salt of a synthetic crystalline aluminosilicate that has a carbon dioxide adsorption amount of 50 μmol/g or less and an average pore size of 3 Å to remove water from the crude linear saturated fluorohydrocarbon compound.

It is preferable that the linear saturated fluorohydrocarbon compound be a linear saturated fluorohydrocarbon compound in which a fluorine atom is not bonded to a terminal carbon atom. It is more preferable that the linear saturated fluorohydrocarbon compound be a compound selected from the group consisting of 2-fluorobutane, 2-methyl-2-fluoropropane, and 2-fluoropentane. It is particularly preferable that the linear saturated fluorohydrocarbon compound be 2-fluorobutane.

DESCRIPTION OF EMBODIMENTS

A purification method according to one embodiment of the invention includes bringing a crude linear saturated fluorohydrocarbon compound represented by $C_4H_9F$ or $C_5H_{11}F$ into contact with a hydrous metal salt of a synthetic crystalline aluminosilicate that has a carbon dioxide adsorption amount of 50 μmol/g or less and an average pore size of 3 Å to remove water from the crude linear saturated fluorohydrocarbon compound.

The purification method according to one embodiment of the invention can reduce or suppress the production of a dehydrofluorinated compound due to a decomposition reaction, and efficiently remove water.

Note that the purity of the fluorohydrocarbon compound that is subjected to purification and the content of a dehydrofluorinated compound refer to values calculated from a peak area determined by gas chromatography that utilizes a flame ionization detector (FID). The water content in the fluorohydrocarbon compound refers to a value determined by FT-IR.

The fluorohydrocarbon compound that is subjected to purification is a linear saturated fluorohydrocarbon compound represented by $C_4H_9F$ or $C_5H_{11}F$.

Examples of the linear saturated fluorohydrocarbon compound represented by $C_4H_9F$ or $C_5H_{11}F$ include 1-fluorobutane, 2-fluorobutane, 1-fluoro-2-methylpropane, 2-fluoro-2-methylpropane, 1-fluoropentane, 2-fluoropentane, 3-fluoropentane, 1-fluoro-2-methylbutane, 1-fluoro-3-methylbutane, 2-fluoro-2-methylbutane, 2-fluoro-3-methylbutane, and 1-fluoro-2,2-dimethylpropane. It is preferable that the linear saturated fluorohydrocarbon compound be a linear saturated fluorohydrocarbon compound selected from the group consisting of 2-fluorobutane, 2-fluoro-2-methylpropane, and 2-fluoropentane, and particularly preferably 2-fluorobutane, since the advantageous effects of the invention can be more significantly achieved.

These fluorohydrocarbon compounds are known compounds. The term "crude fluorohydrocarbon compound" used herein refers to the purification target that is brought into contact with the hydrous metal salt of a synthetic crystalline aluminosilicate. A crude compound described below is normally used as the crude fluorohydrocarbon compound. Note that the crude fluorohydrocarbon compound that is brought into contact with the hydrous metal salt of a synthetic crystalline aluminosilicate may have been purified using another purification method. The fluorohydrocarbon compound may be repeatedly purified using the purification method according to one embodiment of the invention.

The crude fluorohydrocarbon compound used in connection with one embodiment of the invention includes a trace amount of a dehydrofluorinated compound, water, and the like in addition to the linear saturated fluorohydrocarbon compound represented by $C_4H_9F$ or $C_5H_{11}F$. The content of a dehydrofluorinated compound in the crude fluorohydrocarbon compound is normally 0.01 to 0.1 vol %, and preferably 0.02 to 0.05 vol %.

The content of water in the crude fluorohydrocarbon compound (i.e., the content of water in the crude fluorohydrocarbon compound that has not been brought into contact with the hydrous metal salt of a synthetic crystalline aluminosilicate) is normally 100 to 5,000 vppm, and preferably 100 to 3,000 vppm.

The crude fluorohydrocarbon compound used in connection with one embodiment of the invention may be produced (obtained) using a known production method. For example, crude 2-fluorobutane may be produced (obtained) using the method described in J. Org. Chem, 44 (22), 3872 (1987). A commercially-available product may also be used as the crude fluorohydrocarbon compound.

The hydrous metal salt (MS) of the synthetic crystalline aluminosilicate used in connection with one embodiment of the invention is a molecular sieve (MS3A) having an average pore size of 3 Å. An MS is normally known as a solid acid. An MS having a carbon dioxide adsorption amount of 50 μmol/g or less, preferably 40 μmol/g or less, and more preferably 30 μmol/g or less, is used since it is possible to reduce or suppress the production of a dehydrofluorinated compound due to a decomposition reaction or the like while efficiently removing water even when the fluorohydrocarbon compound is brought into contact with the MS. Note that the carbon dioxide adsorption amount is measured using the method described later in connection with the examples.

The hydrous metal salt of a synthetic crystalline aluminosilicate that has a carbon dioxide adsorption amount of 50 μmol/g or less and an average pore size of 3 Å is a known substance, and may be produced (obtained) using a known method. A commercially-available hydrous metal salt of a synthetic crystalline aluminosilicate that has a carbon dioxide adsorption amount of 50 μmol/g or less and an average pore size of 3 Å may be used directly.

A hydrous metal salt of a synthetic crystalline aluminosilicate is sold on the market in various forms (e.g., pellet, trisiv, bead, and powder). It is preferable to use a pellet-like hydrous metal salt of a synthetic crystalline aluminosilicate, more preferably a pellet-like hydrous metal salt of a synthetic crystalline aluminosilicate having a diameter of 1 to 4 mm, and still more preferably a pellet-like hydrous metal salt of a synthetic crystalline aluminosilicate having a diameter of 1.5 to 3.5 mm, from the viewpoint of a dehydrating effect and handling capability.

The hydrous metal salt of a synthetic crystalline aluminosilicate may optionally be activated before use.

The hydrous metal salt of a synthetic crystalline aluminosilicate is preferably used in a ratio of 5 to 80 parts by weight, and more preferably 10 to 50 parts by weight, based on 100 parts by weight of the fluorohydrocarbon compound. If the hydrous metal salt of a synthetic crystalline aluminosilicate is used in too small a ratio, the dehydration performance tends to deteriorate. If the hydrous metal salt of a synthetic crystalline aluminosilicate is used in too large a ratio, a decrease in productivity occurs although an improvement in effect is not achieved.

The crude fluorohydrocarbon compound may be brought into contact with the hydrous metal salt of a synthetic crystalline aluminosilicate using (1) an immersion method that puts the crude fluorohydrocarbon compound in a container that holds the hydrous metal salt of a synthetic crystalline aluminosilicate, and allows the mixture to stand, (2) a circulation method that circulates the crude fluorohydrocarbon compound through a pipe charged with the hydrous metal salt of a synthetic crystalline aluminosilicate to bring the crude fluorohydrocarbon compound into contact with the hydrous metal salt of a synthetic crystalline aluminosilicate, or the like. An appropriate method may be selected from the immersion method, the circulation method, and the like.

The temperature at which the crude fluorohydrocarbon compound is brought into contact with the hydrous metal salt of a synthetic crystalline aluminosilicate is determined taking account of the boiling point of the fluorohydrocarbon compound. If the crude fluorohydrocarbon compound is brought into contact with the hydrous metal salt of a synthetic crystalline aluminosilicate at a temperature higher than the boiling point of the fluorohydrocarbon compound, a decrease in yield may occur. Therefore, it is preferable to bring the cmde fluorohydrocarbon compound into contact with the hydrous metal salt of a synthetic crystalline aluminosilicate at a temperature lower than the boiling point of the fluorohydrocarbon compound. The temperature at which the crude fluorohydrocarbon compound is brought into contact with the hydrous metal salt of a synthetic crystalline aluminosilicate is preferably 0 to 50° C., and more preferably 0 to 30° C., from the viewpoint of productivity.

The crude fluorohydrocarbon compound is normally brought into contact with the hydrous metal salt of a synthetic crystalline aluminosilicate for 1 to 72 hours.

Examples of a dehydrofluorinated compound that is produced due to a decomposition reaction that may occur when the crude fluorohydrocarbon compound is brought into contact with the hydrous metal salt of a synthetic crystalline aluminosilicate include (E)-2-butene, (Z)-2-butene, and 1-butene (when 2-fluorobutane is used as the fluorohydrocarbon compound).

The purification method according to one embodiment of the invention can reduce or suppress the production of a dehydrofluorinated compound due to a decomposition reaction, and efficiently remove water.

The content of a dehydrofluorinated compound in the purified fluorohydrocarbon compound obtained by bringing the crude fluorohydrocarbon compound into contact with the hydrous metal salt of a synthetic crystalline aluminosilicate is preferably 0.1% or less, and more preferably 0.05% or less.

The purity of the purified fluorohydrocarbon compound is normally 99.90 vol % or more, and preferably 99.95 vol % or more.

The content of water in the purified fluorohydrocarbon compound (i.e., the content of water in the purified fluorohydrocarbon compound that has been brought into contact with the hydrous metal salt of a synthetic crystalline aluminosilicate) is normally 50 vppm or less, preferably 30 or less vppm, and more preferably 20 vppm or less.

EXAMPLES

The invention is further described below by way of examples. Note that the invention is not limited to the following examples.

The analysis methods used in connection with the examples are described below.
(1) Measurement of Carbon Dioxide Adsorption amount of Hydrous Metal Salt of Synthetic Crystalline Aluminosilicate The carbon dioxide adsorption amount (i.e., the amount of basic sites on a solid surface) of the hydrous metal salt of a synthetic crystalline aluminosilicate was determined using a temperature programmed desorption (TPD) method.

Specifically, the measurement cell of an automatic temperature-programmed desorption spectrometer ("TPD-1-ATw" manufactured by BEL Japan, Inc.) was charged with 0.1 g of the hydrous metal salt of a synthetic crystalline aluminosilicate. After passing helium gas including carbon dioxide (0.5 vol %) through the measurement cell (flow rate: 100 ml/min) at 100° C. for 30 minutes, helium gas was passed through the measurement cell (flow rate: 50 ml/min) for 30 minutes. The temperature was then increased to 800° C. at a heating rate of 10° C/min, and the total carbon dioxide desorption amount was taken as the carbon dioxide adsorption amount (imol/g) of the hydrous metal salt of a synthetic crystalline aluminosilicate.
(2) Measurement of Content of Dehydrofluorinated Compound The content of a dehydrofluorinated compound in the (crude) fluorohydrocarbon compound (before and after immersion) was calculated from the peak area determined by gas chromatography.

The gas chromatography (GC) analysis conditions were as follows.
Device: Agilent (registered trademark) 7890A manufactured by Agilent Technologies Column: Inert Cap (registered trademark) 1 manufactured by GL Sciences Inc. (length: 60 m, inner diameter 0.25 mm, thickness: 1.5 μm)
Column temperature: The column was held at 40° C. for 20 minutes.
Injection temperature: 80° C.
Carrier gas: nitrogen
Split ratio: 40/1
Detector: FID
(3) Measurement of Content of Water The content (vppm: volumetric parts per million) of water in the (chide) fluorohydrocarbon compound (before and after immersion) was determined by FTIR. Measurement device: FTIR spectrometer ("IG-1000" manufactured by Otsuka Electronics Co., Ltd.)
Cell length: 10 m Example 1

A glass ampoule was charged with 5 g of a molecular sieve MS3A(A) having an average pore size of 3 Å ("ZEOLUM (registered trademark) A3" manufactured by Tosoh Corporation) and 20 g of 2-fluorobutane, and the molecular sieve was immersed in 2-fluorobutane at 23° C. for 72 hours. The content of a dehydrofluorinated compound and the content of water in 2-fluorobutane were measured before and after the immersion. The carbon dioxide adsorption amount of the molecular sieve MS3A(A) before the immersion was also measured.

Example 2

A molecular sieve was immersed in 2-fluorobutane in the same manner as in Example 1, except that a molecular sieve MS3A(B) having an average pore size of 3 Å ("Molecular Sieve 3A Pellet 1.6" manufactured by Union Showa K.K.) was used instead of the molecular sieve MS3A(A), The content of a dehydrofluorinated compound, the content of water, and the carbon dioxide adsorption amount of the molecular sieve MS3A(B) (before immersion) were measured in the same manner as described above.

Comparative Example 1

A molecular sieve was immersed in 2-fluorobutane in the same manner as in Example 1, except that a molecular sieve MS3A(C) having an average pore size of 3 Å (manufactured by Wako Pure Chemical Industries, Ltd.) was used instead of the molecular sieve MS3A(A). The content of a dehydrofluorinated compound, the content of water, and the carbon dioxide adsorption amount of the molecular sieve MS3A(C) (before immersion) were measured in the same manner as described above.

Comparative Example 2

A molecular sieve was immersed in 2-fluorobutane in the same manner as in Example 1, except that a molecular sieve MS3A(D) having an average pore size of 3 Å ("MIZUKASIEVES (registered trademark) 3A" manufactured by Mizusawa Industrial Chemicals, Ltd.) was used instead of the molecular sieve MS3A(A). The content of a dehydrofluorinated compound, the content of water, and the carbon dioxide adsorption amount of the molecular sieve MS3A(D) (before immersion) were measured in the same manner as described above.

Comparative Example 3

A molecular sieve was immersed in 2-fluorobutane in the same manner as in Example 1, except that a molecular sieve MS4A having an average pore size of 4 Å ("Molecular Sieve 4A Pellet 1.6" manufactured by Union Showa K.K.) was used instead of the molecular sieve MS3A(A). The content of a dehydrofluorinated compound, the content of water, and the carbon dioxide adsorption amount of the molecular sieve MS4A (before immersion) were measured in the same manner as described above.

Comparative Example 4

A molecular sieve was immersed in 2-fluorobutane in the same manner as in Example 1, except that a molecular sieve MS5A having an average pore size of 5 Å ("Molecular Sieve 5A Pellet 1.6" manufactured by Union Showa K.K.) was used instead of the molecular sieve MS3A(A). The content of a dehydrofluorinated compound, the content of water, and the carbon dioxide adsorption amount of the molecular sieve MS5A (before immersion) were measured in the same manner as described above.

Example 3

A molecular sieve was immersed in 2-methyl-2-fluoropropane (instead of 2-fluorobutane) in the same manner as in Example 1. The content of a dehydrofluorinated compound, the content of water, and the carbon dioxide adsorption amount were measured in the same manner as described above.

Comparative Example 5

A molecular sieve was immersed in 2-methyl-2-fluoropropane in the same manner as in Example 3, except that the molecular sieve MS3A(C) was used instead of the molecular sieve MS3A(A). The content of a dehydrofluorinated compound, the content of water, and the carbon dioxide adsorption amount of the molecular sieve MS3A(C) (before immersion) were measured in the same manner as described above.

Example 4

A molecular sieve was immersed in 2-fluoropentane (instead of 2-fluorobutane) in the same manner as in Example 1. The content of a dehydrofluorinated compound, the content of water, and the carbon dioxide adsorption amount of the molecular sieve MS3A(A) (before immersion) were measured in the same manner as described above.

Comparative Example 6

A molecular sieve was immersed in 2-fluoropentane in the same manner as in Example 4, except that the molecular sieve MS3A(C) was used instead of the molecular sieve MS3A(A). The content of a dehydrofluorinated compound, the content of water, and the carbon dioxide adsorption amount of the molecular sieve MS3A(C) (before immersion) were measured in the same manner as described above.

The results obtained in Examples 1 to 4 and Comparative Examples 1 to 6 are shown in Table 1.

TABLE 1

| | Purification target compound | Adsorbent | Carbon dioxide adsorption amount ($\mu$mol/g) | Content of dehydrofluorinated compound (%) | | Content of water (vppm) | |
|---|---|---|---|---|---|---|---|
| | | | | Before immersion | After immersion | Before immersion | After immersion |
| Example 1 | 2-Fluorobutane | MS3A(A) | 25 | 0.04 | 0.04 | 2,457 | 10 |
| Example 2 | | MS3A(B) | 18 | 0.02 | 0.02 | 2,930 | 8 |
| Comparative Example 1 | | MS3A(C) | 314 | 0.02 | 1.37 | 2,930 | 12 |
| Comparative Example 2 | | MS3A(D) | 151 | 0.04 | 0.42 | 2,457 | 9 |
| Comparative Example 3 | | MS4A | 32 | 0.02 | 4.10 | 2,930 | 8 |
| Comparative Example 4 | | MS5A | 128 | 0.02 | 20.19 | 2,930 | 9 |
| Example 3 | 2-Methyl-2-fluoropropane | MS3A(A) | 25 | 0.07 | 0.08 | 2,120 | 22 |
| Comparative Example 5 | | MS3A(C) | 314 | 0.08 | 2.23 | 2,120 | 25 |
| Example 4 | 2-Fluoropentane | MS3A(A) | 25 | 0.06 | 0.06 | 2,014 | 21 |
| Comparative Example 6 | | MS3A(C) | 314 | 0.07 | 2.15 | 2,014 | 27 |

As is clear from the results shown in Table 1, when a linear saturated fluorohydrocarbon compound represented by $C_4H_9F$ or $C_5H_{11}F$ was brought into contact with the molecular sieve MS3A (i.e., an MS having an average pore size of 3 Å) having a carbon dioxide adsorption amount of 50 $\mu$mol/g or less, it was possible to reduce or suppress the production of a dehydrofluorinated compound due to a decomposition reaction or the like while efficiently removing water (Examples 1 to 4).

When the linear saturated fluorohydrocarbon compound was brought into contact with the molecular sieve MS3A having a carbon dioxide adsorption amount of 50 $\mu$mol/g or more, the content of a dehydrofluorinated compound increased due to immersion (Comparative Examples 1, 2, 5, and 6). When the linear saturated fluorohydrocarbon compound was brought into contact with the molecular sieve MS4A (i.e., an MS having an average pore size of 4 Å) or the molecular sieve MS5A (i.e., an MS having an average pore size of 5 Å), the content of a dehydrofluorinated compound increased due to immersion independently of the carbon dioxide adsorption amount (Comparative Examples 3 and 4).

The invention claimed is:

1. A method for purifying a linear saturated fluorohydrocarbon compound comprising bringing a crude linear saturated fluorohydrocarbon compound represented by $C_4H_9F$ or $C_5H_{11}F$ into contact with a hydrous metal salt of a synthetic crystalline aluminosilicate that has a carbon dioxide adsorption amount of 50 μmol/g or less and an average pore size of 3 Å to remove water from the crude linear saturated fluorohydrocarbon compound.

2. The method according to claim 1, wherein the linear saturated fluorohydrocarbon compound is a linear saturated fluorohydrocarbon compound in which a fluorine atom is not bonded to a terminal carbon atom.

3. The method according to claim 1, wherein the linear saturated fluorohydrocarbon compound is a compound selected from a group consisting of 2fluorobutane, 2-methyl-2-fluoropropane, and 2-fluoropentane.

4. The method according to claim 1, wherein the linear saturated fluorohydrocarbon compound is 2-fluorobutane.

* * * * *